(12) United States Patent
Neumann

(10) Patent No.: US 12,039,420 B2
(45) Date of Patent: Jul. 16, 2024

(54) SYSTEM AND METHOD FOR GENERATING A DIRECTION INQUIRY RESPONSE FROM BIOLOGICAL EXTRACTIONS USING MACHINE LEARNING

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 959 days.

(21) Appl. No.: 17/032,115

(22) Filed: Sep. 25, 2020

(65) Prior Publication Data

US 2022/0101176 A1    Mar. 31, 2022

(51) Int. Cl.
| | | |
|---|---|---|
| G06N 20/00 | (2019.01) | |
| A61B 5/16 | (2006.01) | |
| G06F 16/955 | (2019.01) | |
| G06F 18/214 | (2023.01) | |
| G16B 5/00 | (2019.01) | |

(52) U.S. Cl.
CPC ............. *G06N 20/00* (2019.01); *A61B 5/165* (2013.01); *G06F 16/9558* (2019.01); *G06F 18/214* (2023.01); *G16B 5/00* (2019.02)

(58) Field of Classification Search
CPC ... G06N 20/00; G06F 16/9558; G06F 18/214; G16B 5/00; A61B 5/165
See application file for complete search history.

(56) References Cited

U.S. PATENT DOCUMENTS

| | | | |
|---|---|---|---|
| 7,080,057 | B2 | 7/2006 | Scarborough |
| 7,310,626 | B2 | 12/2007 | Scarborough |
| 7,343,197 | B2 | 3/2008 | Shusterman |
| 7,558,767 | B2 | 7/2009 | Scarborough |
| 7,562,059 | B2 | 7/2009 | Scarborough |
| 7,874,983 | B2 | 1/2011 | Zancho |
| 8,038,614 | B2 | 10/2011 | Gobeyn |
| 8,038,615 | B2 | 10/2011 | Gobeyn |
| 8,046,251 | B2 | 10/2011 | Scarborough |
| 8,831,299 | B2 | 9/2014 | Kurtz |
| 9,693,696 | B2 | 7/2017 | Kovacs |
| 10,159,411 | B2 | 1/2018 | Tzvieli |
| 2013/0231947 | A1* | 9/2013 | Shusterman ........... G16H 40/67 705/2 |

(Continued)

*Primary Examiner* — David E Choi
(74) *Attorney, Agent, or Firm* — Caldwell Intellectual Property Law

(57) ABSTRACT

A system generating a directional inquiry response is disclosed. The system comprises a computing device configured to receive a directional inquiry from a device operated by a user. Computing device is configured to retrieve a biological extraction from the user and generate a directional inquiry response by training a machine-learning process using directional training data correlating a plurality of biological extractions to a plurality of directions and generating the directional inquiry response as a function of the biological extraction from the user and the machine-learning process. Computing device is configured to update the directional inquiry response as a function of the preferences of the use and output the updated directional inquiry response to the device operated by the user. A method for generating a directional inquiry response is also disclosed.

20 Claims, 6 Drawing Sheets

(56) References Cited

U.S. PATENT DOCUMENTS

| | | | |
|---|---|---|---|
| 2018/0121784 A1* | 5/2018 | Ichiboshi | G16H 10/20 |
| 2019/0130361 A1* | 5/2019 | Hazarika | G06Q 10/063112 |
| 2019/0385469 A1 | 12/2019 | Gordon et al. | |
| 2020/0193382 A1* | 6/2020 | Michaels | G06F 40/289 |
| 2020/0302564 A1* | 9/2020 | Varga | G06F 16/24578 |
| 2021/0090027 A1* | 3/2021 | Agashe | G06Q 30/08 |
| 2021/0241137 A1* | 8/2021 | Jain | G16H 10/20 |
| 2021/0343376 A1* | 11/2021 | Neumann | G06Q 50/01 |
| 2022/0101176 A1* | 3/2022 | Neumann | G06N 20/00 |

* cited by examiner

SYSTEM AND METHOD FOR GENERATING A DIRECTION INQUIRY RESPONSE FROM BIOLOGICAL EXTRACTIONS USING MACHINE LEARNING

FIELD OF THE INVENTION

The present invention generally relates to the field of machine learning. In particular, the present invention is directed to systems and methods for generating directional inquiry responses from a biological extraction using machine learning.

BACKGROUND

Efficient routing of inquiries to responses regarding directional requests remains elusive, because of the divergent criteria according to which such routing may be determined; data complexity can obscure algorithmic techniques. A resulting lack of specificity may end in dissatisfaction with resulting outputs.

SUMMARY OF THE DISCLOSURE

In an aspect, a system for generating a directional inquiry response using machine learning includes a computing device configured to receive a directional inquiry from a device operated by a user. Computing device is configured to retrieve a biological extraction from the user and generate a directional inquiry response by training a machine-learning process using directional training data correlating a plurality of biological extractions to a plurality of directions and generating the directional inquiry response as a function of the biological extraction from the user and the machine-learning process. Computing device is configured to update the directional inquiry response as a function of the preferences of the use and output the updated directional inquiry response to the device operated by the user.

In another aspect, a method for generating a directional inquiry response using machine learning is disclosed. The method receives a directional inquiry from a device operated by a user and retrieves a biological extraction from the user. The method generates directional inquiry response by training a machine-learning process using directional training data correlating a plurality of biological extractions to a plurality of directions and generating the directional inquiry response as a function of the biological extraction from the user and the machine-learning process. The method updates the directional inquiry response as a function of the preferences of the use and output the updated directional inquiry response to the device operated by the user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a direction inquiry response based on a biological extraction, using machine learning, where machine-learning models therefor may be generated, using machine-learning processes operating on training examples. A directional inquiry is received from a user along with a biological extraction. A trained machine-learning process is used to generate a directional inquiry response which is updated based on the user's preference. Machine-learning processes may include, without limitation, classification, regression, and/or neural network processes, which may perform unsupervised or supervised machine-learning procedures including naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. The directional inquiry response is then sent to the user-client device.

Figure 1:
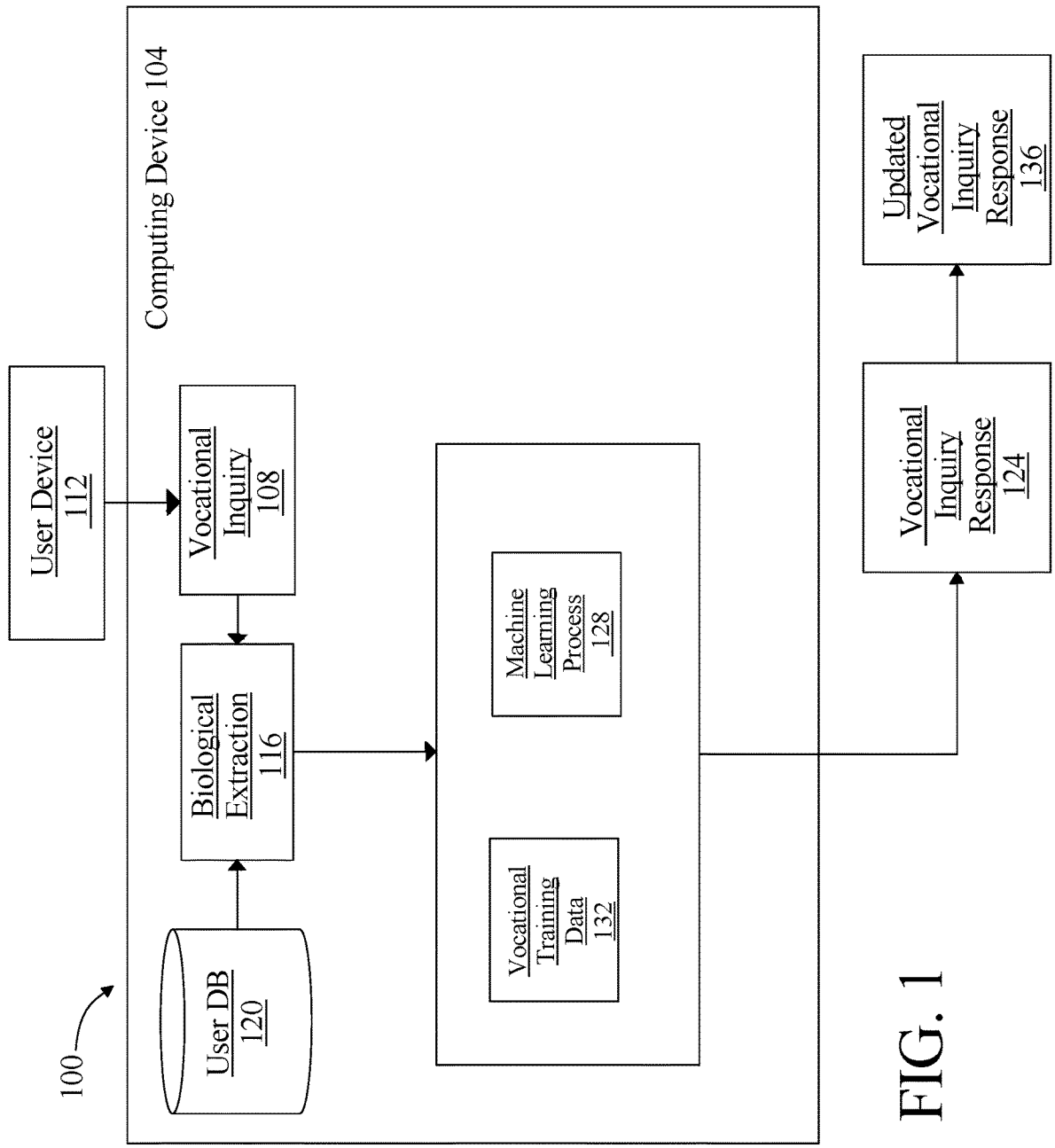
FIG. 1 is a block diagram of illustrating an exemplary embodiment of the system for generating a directional inquiry response.

Referring now to FIG. 1, an exemplary embodiment of a system 100 for generating a direction inquiry response is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 receives a direction inquiry 108 from a device of user 112. As used in this specification, a "directional inquiry" is defined as a request for advice about a career, a job, or an area of interest where a user may be drawn, or for which they are suited, trained, or qualified; a direction inquiry may correspond to a direction in which a person may take a career or the like. A directional inquiry 108 may include an interest on a paid position, a voluntary position, an internship, a fellowship, and the like. A voluntary inquiry 108 may include an interest on a full time or a part time position. For example, a user may find that they are drawn to working with automobiles. After entering such an interest in the user-client device, the user may receive a directional inquiry response that may match the user with a career as a mechanic. As another example, a similar interest in automobiles may result in a directional inquiry response of a direction as a car salesperson. As used in this disclosure, a "directional inquiry response" is a match made between a directional inquiry and a career, a job, or an area of interest where a user may be drawn to or for which they may be trained or successful. A directional inquiry 108 may include an interest in a religious life. For example, an interest in a religious direction may generate a direction such as becoming a Roman Catholic priest, a Rabbi, an Iman, a Nun, or other possible directions that involve religion. A directional inquiry 108 may be received from a user-client device. As used in this disclosure, a "device of user" is any device capable of supporting a request from a user in creating a directional inquiry 108. User-client device 112 may include any type of telephonic device, such as, but not limited to a mobile phone, a smartphone, a telephone connected to a local area network line, and the like. User-client device 112 may include other devices capable such as, but not limited to a laptop computer, a tablet computer, a desktop computer, and the like. User-client device 112 may include voice-controlled intelligent personal assistance modules, or the like. Further examples of user-client device 112 will be apparent to persons of skill in the art upon reading the entirety of this disclosure, and may include, without limitation, an interactive chatterbot configured in, for example, a smartphone to interact with the user.

With continued reference to FIG. 1, computing device 104 is configured to retrieve a biological extraction 116 from the user. A "biological extraction" as used in this disclosure is an element of data including at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction 116 may include a psychological profile; the psychological profile may be obtained utilizing a questionnaire performed by the user.

Still referring to FIG. 1, in an embodiment, physiological state data may include genomic and/or genetic data, including deoxyribonucleic acid (DNA) samples and/or sequences, such as without limitation DNA sequences or other genetic sequences contained in one or more chromosomes in human cells. As defined in this specification, "genetic data" is defined as data from the user relating to the inherited or acquired genes of a person. "Genomic data," as used in this disclosure is defined as the study of all the genes from a user including interaction of those genes with each other and with the environment of the user. Genomic and/or genetic data may include, without limitation, ribonucleic acid (RNA) samples and/or sequences, such as samples and/or sequences of messenger RNA (mRNA) or the like taken from human cells. Genetic data may include telomere lengths. Genomic and/or genetic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any mental state data. As used in this disclosure, a "mental state data" is data describing a state of mind from the user. A mental state of mind may include information about how the user currently feels at the time of the directional inquiry. Factors such as the user's home life, present environment, or the like may affect the state of mind of the user. In addition, the state of mind of the user may be affected by external factors which may include, but are not limited to medications the user is taking, world events that may impact how the user feels mentally, and events in the user's life that may have an impact in the user's mental health such as the death of a family member. Mental state data may include, without limitation, any psychiatric medical data available from the user. Psychiatric data may be used to, for example, avoid a direction inquiry request that may trigger a known/diagnosed mental anomaly. Mental state data may include self-reported paradigmatic states of mind such as, but not limited to love, hate, pleasure, and pain. A mental state may refer to a particular interest or career, for example, the user may feel hated towards the military which may be a factor considered with the directional inquiry request where the computing device may use the mental state to either suggest or eliminate a directional inquiry request response. Mental state data may be self-reported by the user. For example, a user may state how they feel at the time they seek information about a direction. The user may also enter a diagnosis about a mental condition that have obtained from a health provider such as a physician or a psychologist.

Still referring to FIG. 1, computing device 104 may be configured generate using tendency training data correlating mental state data with tendency data and a second machine-learning process, a tendency model. As used in this disclosure, a "tendency model" is defined as how a user behavior may be influenced by certain factors. Factors may include, but not limited to psychological, mental states, social, contextual factors which may include, emotions, habits, routines, and the like. As defined in this disclosure, "tendency data" is data produced as a result of actions by the user, which may include, without limitation, commercial behavior, visits to websites, types of music listened by the user, social media interactions, types of mobile applications installed, and the like. Tendency data may be collected using, for example, surveys, questionnaires, marketing studies, and the like. The machine-learning process and the use of training data will be described further in this disclosure.

Alternative or additionally, and with continued reference to FIG. 1, computing device 104 may be configured to generate a priority value as a function of the directional inquiry response and the tendency model. As used in this disclosure, a "priority value" is defined as a ranking of a direction based on a directional inquiry response and a tendency model for the user. As a non-limiting example, a tendency model for a user may be generated where the user is likely to do well in a job or a career that surrounds them with children. As such, careers such as, for example, a pediatrician or a schoolteacher may receive a higher priority score than a career where the user is not surrounded by people or not surrounded by children. A priority value may include a numerical score on a scale from 1 to 10, where, as in our example, a schoolteacher may receive a score of 10, while a career such as a college professor may receive a lower score. The user may select a filter to remove any priority values that are below a threshold selected by the user. In an embodiment, the computing device is further configured to sort the priority values in descending order. For example, a user may sort the data and view the scores from the highest reported value to the lowest.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, tendency, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Still referring to FIG. 1, retrieval of biological extraction 108 may include, without limitation, reception of biological extraction 108 from another computing device 104 such as a device operated by a medical and/or diagnostic professional and/or entity, a device operated by the user, and/or any device suitable for use as a third-party device as described in further detail below. Biological extraction 108 may be received via a questionnaire posted and/or displayed on a third-party device as described below, inputs to which may be processed as described in further detail below. Alternatively or additionally, biological extraction 108 may be stored in and/or retrieved from a user database 112. User database 120 may include any data structure for ordered storage and retrieval of data, which may be implemented as a hardware or software module. A user database 120 may be implemented, without limitation, as a relational database, a key-value retrieval datastore such as a NOSQL database, or any other format or structure for use as a datastore that a person skilled in the art would recognize as suitable upon review of the entirety of this disclosure. A user database 120 may include a plurality of data entries and/or records corresponding to user tests as described above. Data entries in a user database 120 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 120 may reflect categories, cohorts, and/or populations of data consistently with this disclosure. User database 120 may be located in memory of computing device 104 and/or on another device in and/or in communication with system 100.

Figure 2:
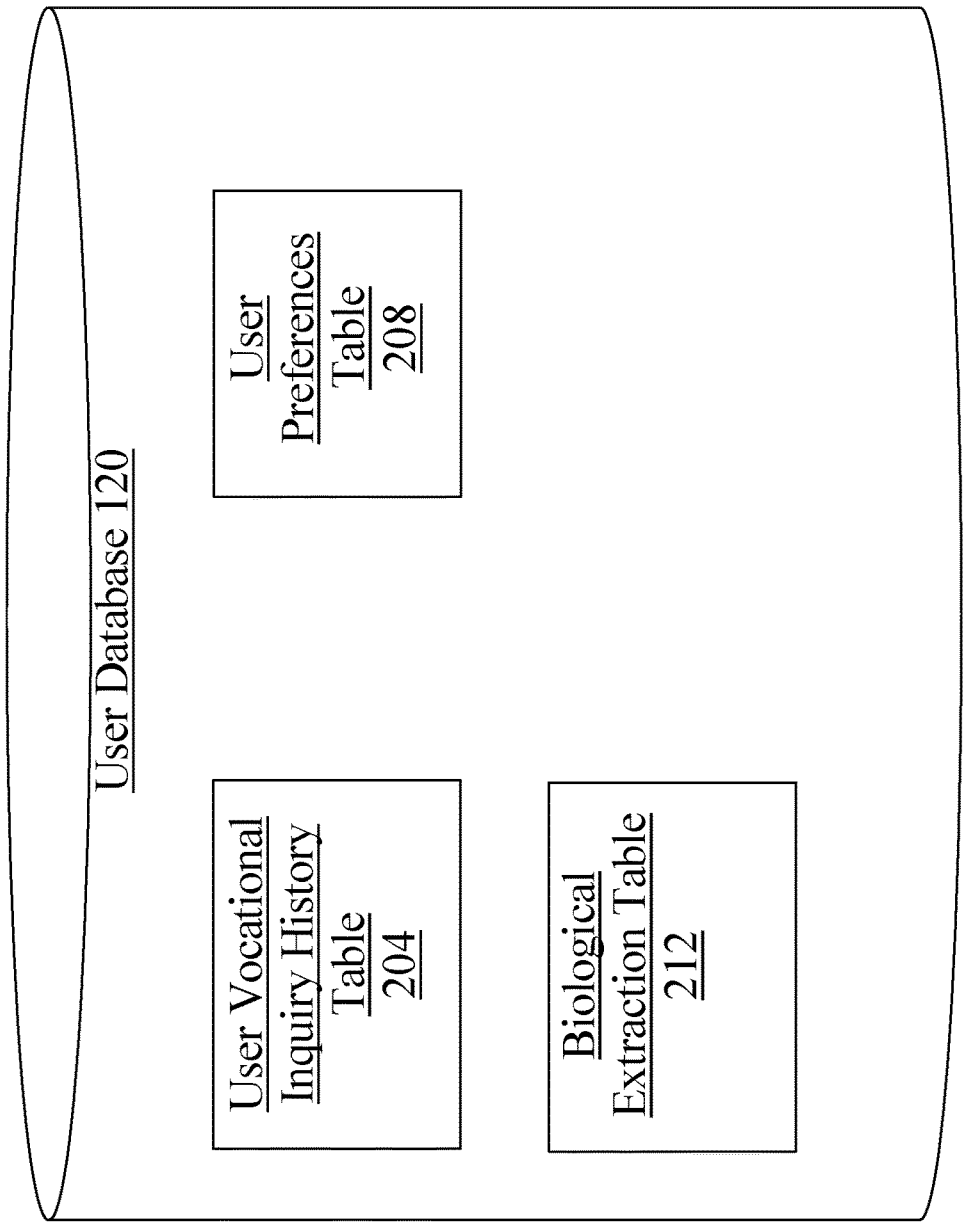
FIG. 2 is a block diagram illustrating an exemplary embodiment of a user database.

Referring now to FIG. 2, an exemplary embodiment of a user database 120 is illustrated. One or more tables in user database 120 may include, without limitation, a user directional inquiry history table 204, which may be used to store data describing past user requests, educational activities, employment history, prior directional inquiry response 124, or the like. One or more tables in user database 120 may include, without limitation, user preference table 208, which may be used to store one or more user preferences regarding type of employment, interests, or the like. One or more tables in user database 120 may include, without limitation, a biological extraction table 212, which may be used to store biological extraction data 116. Persons skilled in the art, upon reviewing the entirety of this disclosure, will be aware of various alternative or additional data which may be stored in user database 120, including without limitation any data concerning any user activity, demographics, profile information, viewing and/or media consumption history, or the like.

With continued reference to FIG. 1, computing device 104 may be configured to generate a directional inquiry response 124; this may be accomplished, without limitation, using machine learning. A machine-learning process 128 may be trained using directional training data 132 correlating a plurality of biological extractions to a plurality of directions. Computing device may be configured to output the directional inquiry response 124 as a function of the biological extraction 116 from the user and the machine-learning process 128. A "machine learning process" is a process that automatedly uses a body of data known as "training data" and/or a "training set" to generate an algorithm that will be performed by a computing device 104/module to produce outputs given data provided as inputs; this is in contrast to a non-machine learning software program where the commands to be executed are determined in advance by a user and written in a programming language. This contrasts with a non-machine learning software program where the commands to be executed are determined in advance by a user and written in a programming language. At least a machine-learning process 128 may be used by computing device 104 to generate an inquiry response as described in further detail below.

Figure 3:
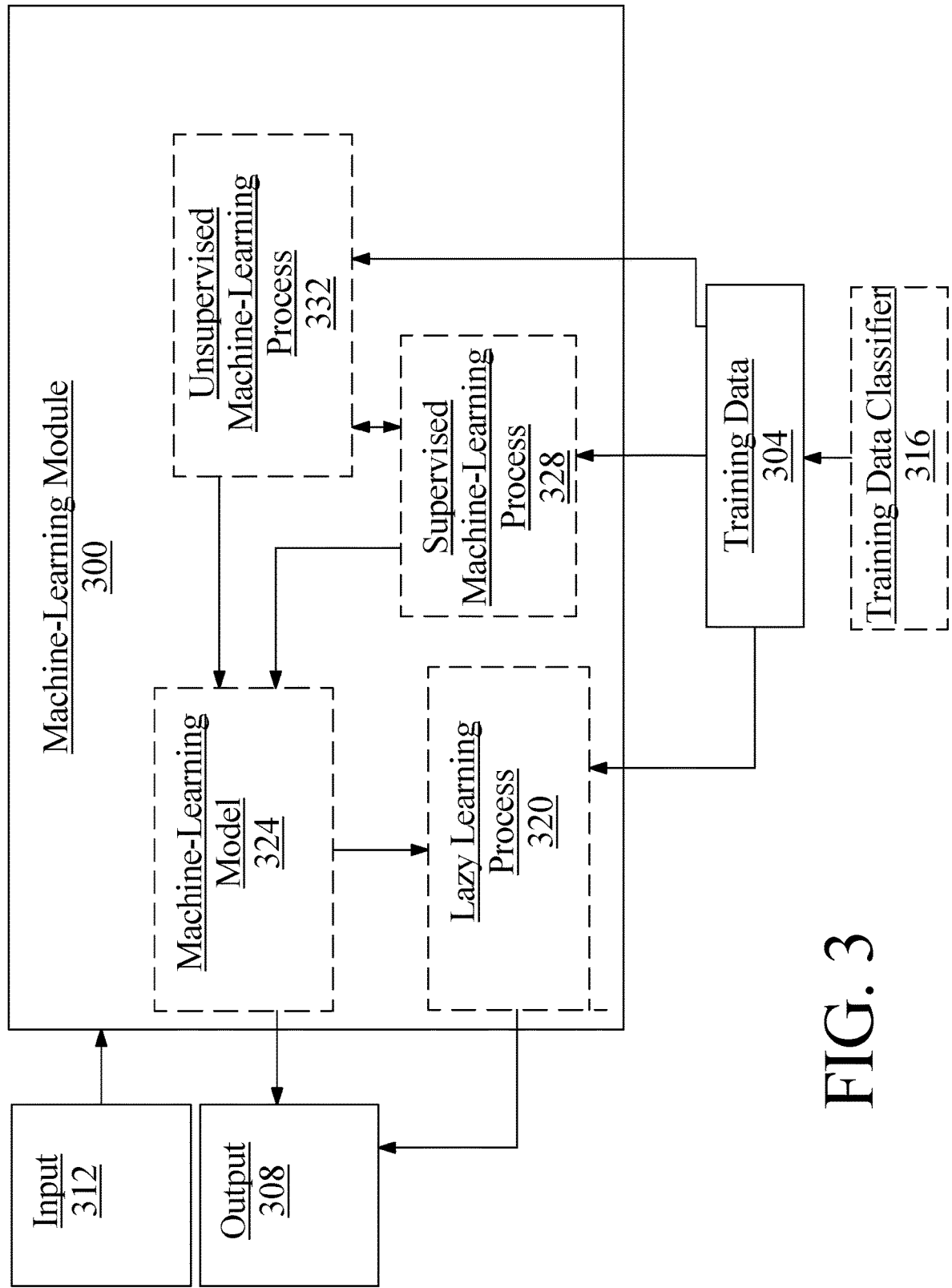
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. In Training data 304 used by machine-learning module 300 may correlate any input data as described in this disclosure to any output data as described in this disclosure. With reference to FIG. 1, directional training data 132 trains a machine learning process 124 where the training data correlates a plurality of biological extraction to a plurality of directions. As a non-limiting illustrative example, the directional inquiry response is the output as a function of the biological extraction 116 from the user and the machine-learning process 128.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to train, for example, a classifier which will then, based on the training data, select a machine-learning process as a function of a biological extraction.

Figure 4:
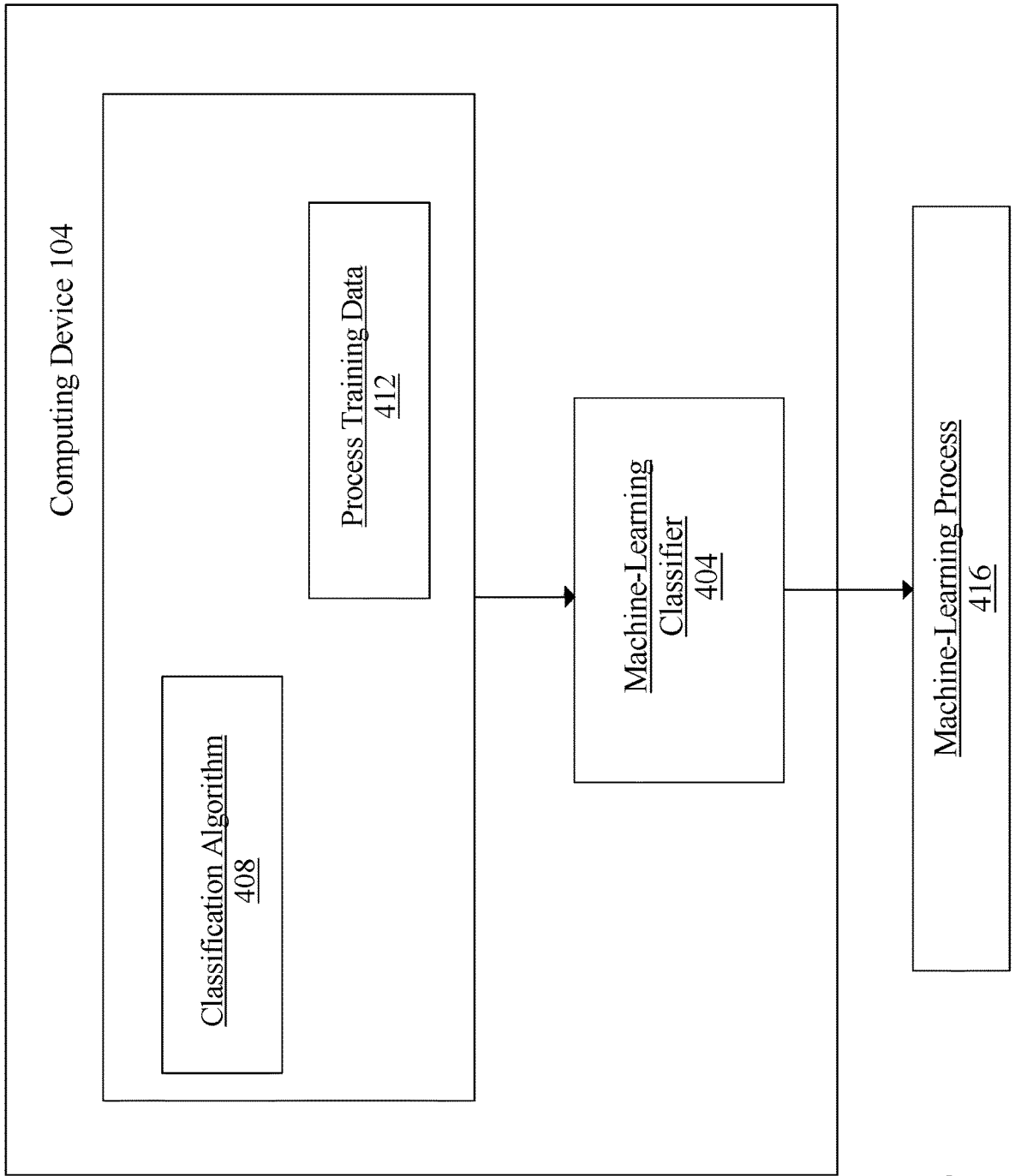
FIG. 4 is a block diagram of an exemplary embodiment of a machine-learning module for generating a directional inquiry response.

Referring now to FIG. 4, in an embodiment, computing device 104 may be configured to generate a directional inquiry response 124 where the computing device 104 is configured to generate a machine-learning classifier 404 as a function of a classification algorithm 408 and process training data 412. The process training data 412 correlates biological extraction to identifiers of a machine-learning process 416. The machine-learning process 416 is then outputted as a function of the biological extraction and the machine-learning classifier 404. As an example, a user suffering from Parkinson's disease may seek a directional inquiry response as to what type of job may be possible for someone with Parkinson's symptoms. Once the machine-learning classifier is trained, a machine-learning process 416 with a k-neighbor algorithm may be outputted which may provide the best accuracy using a biological extraction that incorporates Parkinson's disease. Other machine-learning processes may include, but not limited to decision tree, linear discriminant analysis, support vector machine, and the like.

Referring back to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, machine-learning module 300 may be configured to perform an eager learning process or protocol which may be alternatively known as "instant training." As used in this disclosure, "eager learning" is a process of building a classification model based on the given training data 304 before receiving data for classification. As a result, the process may commit to a single algorithm based on training data 304. For instance, an eager learner may construct a general, input-independent target function during training of the system.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include [input examples] as described above as inputs, [output examples] as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, computing device 104 may be configured to update the directional inquiry response 124 as a function of the preferences of the user 112. As used in this disclosure, a "preference of the user" are themes that a user may choose to sort the directional inquiry responses. Theme may include financial factors such as, but not limited to, income, and potential income potential. Another category may include geographical location such as a particular city, the number of miles away from the user's residence, and the like. For example, the user may prefer to update the directional inquiry response according to an income level. In another non-limiting example, a user may update the directional inquiry response 124 according to their religious beliefs. A user, for example, may be a Jehovah's Witness, and may want to update the directional inquiry response to refine the direction inquiry response to not show any directions performing a blood transfusion. Other non-limiting examples of user preferences may include, updating by the number of hours of work required, a requirement to join a labor union, update to show directions that only work on weekends, and the like. Alternatively, or additionally, a user may update the directional inquiry response by selecting multiple categories. For example, a user may select to view potential directions based on income and distance from a geographical location, such as the residence of the user, that includes a certain range. As a non-limiting example, the user may select a direction of $100,000 where the user may travel up to 30 miles from their residence.

Alternatively, or additionally, computing device 104 may generate a directional inquiry response 124 where the response includes an educational recommendation. Systems and methods for generating educational inquiries and corresponding responses may be implemented, without limitation, as described in U.S. Nonprovisional application Ser. No. 16/825,098, filed on Mar. 20, 2020, and entitled "ARTIFICIAL INTELLIGENCE SYSTEMS AND METHODS FOR GENERATING EDUCATIONAL INQUIRY RESPONSES FROM BIOLOGICAL EXTRACTIONS," which is hereby incorporated by reference in its entirety.

With reference back to FIG. 1, in an embodiment, the preferences of the user may include a type of work experience. As used in this disclosure, a "type of work experience" is defined as a type of career or job placement that user 112 seeks a directional inquiry response 124. For example, user 112 may seek a work shadowing experience. Work shadowing allows user 112 to observe the work of another user giving user 112 an insight into what working life in that career or job or with a particular employer may be like. Another example of a type of job experience may include working abroad. Working abroad would allow user 112 to travel to a foreign country while engaging in employment. Another non-limiting example of a type of work experience may include volunteer work. Volunteer work would expose user 112 to charity work or work in the public sector without the benefit of financial compensation. Other non-limiting examples of types of work experience include part-time work, full time work, an internship, a fellowship, and the like. In an embodiment, computing device 114 may be configured to update an directional inquiry response as a function of the type of work experience With continued reference to FIG. 1, computing device 104 may be configured to output the machine-learning classifier 136 to the device of user 112. The output may include, for example, a response in textual form that may include the directional inquiry response. The output may include contact information for a direction professional such as a job counselor, a life coach, a recruiter, and the like. In an embodiment, the output transmitted to the user includes a plurality of hyperlinks as a function of the machine-learning classifier 136. A hyperlink, as used in this disclosure, is a link from a hypertext file or document to another location or file, typically activated by clicking on a highlighted word or image on the screen. The hyperlinks may include, but not limited to, links to specific websites where more information may be available regarding a particular direction. In another non-limiting example, the hyperlinks may include contact information to agencies that specialize with the direction which is the subject of the response. In another non-limiting example, a hyperlink may contain a link to live help where a professional may appear and answer user 112 questions.

Figure 5:
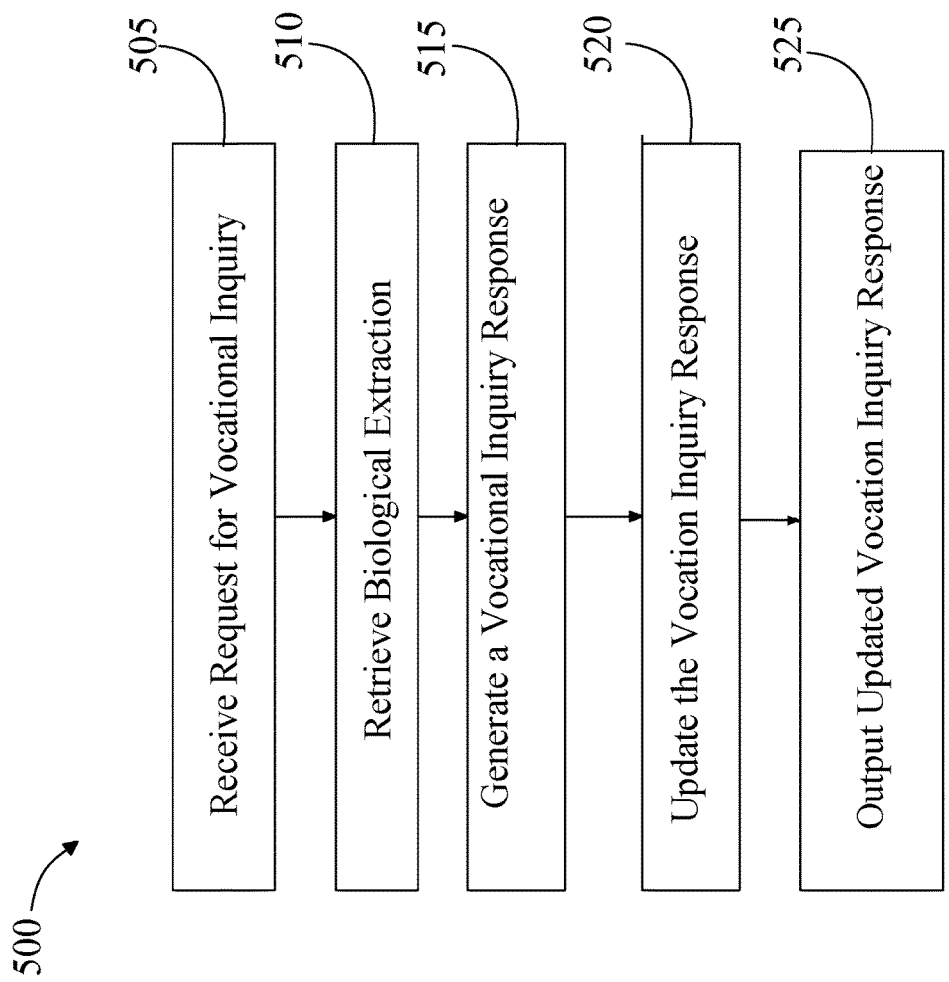
FIG. 5 is a flow diagram illustrating an exemplary embodiment of a method of generating directional inquiry response.

Now with reference to FIG. 5, a method 500 for generating a direction inquiry response is disclosed. At step 505, computing device may receive a request for a directional inquiry from a client device of a user. This may be implemented, without limitation, as described in FIGS. 1-4

With continued reference to FIG. 5, at step 510, computing device retrieves a biological extraction from the user. This may be implemented, without limitation, as described in FIGS. 1-4. Physiological data may include, without limitation any mental state data which may be implemented, without limitation, as described in FIGS. 1-4. A biological extraction may include a generic sequence. Retrieval of biological extraction may include, without limitation, reception of biological extraction from another computing device such as a device operated by a medical and/or diagnostic professional and/or entity, a device operated by the user, and/or any device suitable for use as a third-party device. This may be implemented, without limitation, as described in FIGS. 1-4.

Still referring to FIG. 5, at step 515, computing device may be configured to generate a directional inquiry response. A machine-learning process may be trained using directional training data correlating a plurality of biological extractions to a plurality of directions. Computing device may be configured to output the directional inquiry response as a function of the biological extraction from the user and the machine-learning process. This may be implemented, without limitation, as described in FIGS. 1-4. Computing device may generate using tendency training data correlating mental state data with tendency data and a second machine-learning process, a tendency model. This may be implemented, without limitation, as described in FIGS. 1-4. Computing device may be configured to generate a priority value as a function of the directional inquiry response and the tendency model. This may be implemented, without limitation, as described in FIGS. 1-4. Computing device may be configured to generate a directional inquiry response where the computing device is configured to generate a machine-learning classifier as a function of a classification algorithm and process training data. The process training data correlates biological extraction to identifiers of machine-learning processes. The machine-learning process is then outputted as a function of the biological extraction and the machine-learning classifier. This may be implemented, without limitation, as described in FIGS. 1-4.

At step 520, and still referring to FIG. 5, computing device may be configured to update the directional inquiry response as a function of the preferences of the user. This may be implemented, without limitation, as described in FIGS. 1-4. Computing device may update the directional inquiry response as a function of the type of work experience. This may be implemented, without limitation, as described in FIGS. 1-4.

Still referring to FIG. 5, at step 525, computing device may be configured to output the updated directional inquiry response to the device of user. This may be implemented, without limitation, as described in FIGS. 1-4. In an embodiment, the output transmitted to the user includes a plurality of hyperlinks as a function of the updated directional inquiry response. This may be implemented, without limitation, as described in FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
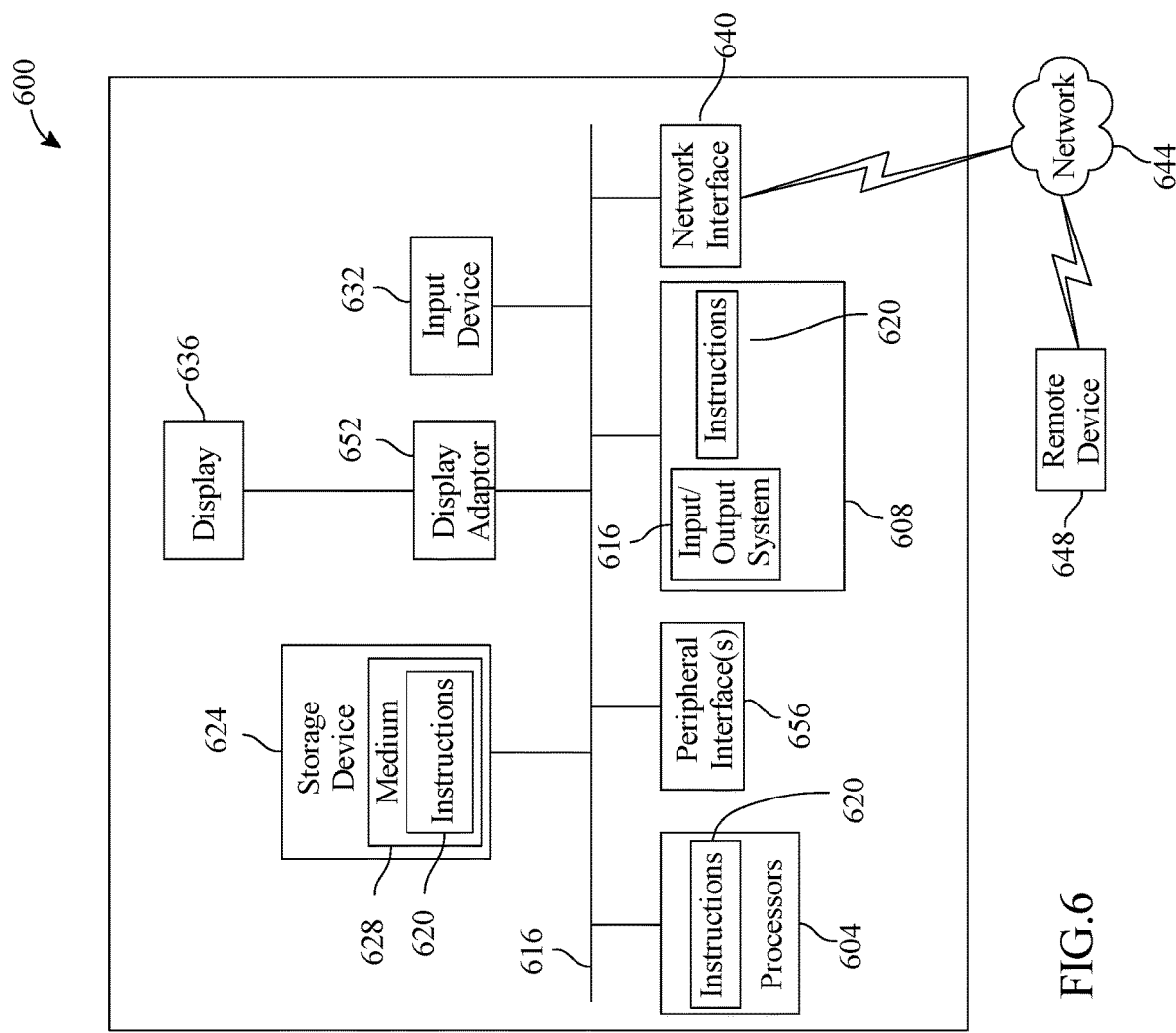
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a direction inquiry response using machine learning, the system comprising:
    a computing device, the computing device configured to:
    retrieve a biological extraction of a user;
    generate a directional inquiry response, wherein generating the directional inquiry response comprises:
        training a machine-learning process using directional training data correlating a plurality of biological extraction to a plurality of directions; and
        generating the directional inquiry response as a function of the biological extraction from the user and the machine-learning process;
    generate a tendency model;
    generate at least one priority value as a function of the directional inquiry response and the tendency model;
    remove a priority value of the at least one priority value as a function of a filter comprising a user-selected threshold value for the at least one priority value; and
    output the directional inquiry response.

2. The system of claim 1, wherein the computing device is further configured to retrieve the biological extraction from a second computing device.

3. The system of claim 1, wherein the biological extraction comprises mental state data.

4. The system of claim 3, wherein the computing device is further configured to:
    generate, using training data correlating mental state data with tendency data and a second machine-learning process, the tendency model.

5. The system of claim 4, wherein the computing device is further configured to sort the priority value in descending order.

6. The system of claim 1, wherein the biological extraction includes a genetic sequence.

7. The system of claim 1, wherein the computing device is further configured to:
    generate a classifier as a function of a classification algorithm and process training data, wherein the process training data correlates biological extractions to identifiers of machine learning processes; and
    output the machine-learning process as a function of the biological extraction and the classifier.

8. The system of claim 1, wherein the computing device is further configured to update the directional inquiry response as a function of a preference of the user.

9. The system of claim 8, wherein the preference of the user comprises a type of work experience.

10. The system of claim 1, wherein the directional inquiry response transmitted to the user includes a plurality of hyperlinks as a function of the updated directional inquiry response.

11. A method for generating a direction inquiry response using machine learning, the method comprising:
    receiving, by a computing device, a request for a directional inquiry from a device operated by a user;
    retrieving, by the computing device, a biological extraction from the user;
    generating, by the computing device, the directional inquiry response, wherein generating a response comprises:
        training a machine-learning process using directional training data correlating a plurality of biological extraction to a plurality of directions; and
        generating the directional inquiry response as a function of the biological extraction from the user and the machine-learning process;
    generating, by the computing device, a tendency model;
    generating, by the computing device, at least one priority value as a function of the directional inquiry response and the tendency model;
    removing, by the computing device, a priority value of the at least one priority value as a function of a filter comprising a user-selected threshold value for the at least one priority value; and
    providing the directional inquiry.

12. The method of claim 11, further comprising receiving the biological extraction from a second computing device.

13. The method of claim 11, wherein the biological extraction comprises mental state data.

14. The method of claim 13, further comprising:
    generating, using training data correlating mental state data with tendency data and a second machine-learning process, the tendency model.

15. The method of claim 14, further comprising sorting the priority value in descending order.

16. The method of claim 11, wherein the biological extraction includes a genetic sequence.

17. The method of claim 11, wherein generating a directional response further comprises:
    generating a machine-learning classifier as a function of a classification algorithm and process training data, wherein the process training data correlates biological extractions to identifiers of machine learning processes; and generating the machine-learning process as a function of the biological extraction and the machine-learning classifier.

18. The method of claim 11, wherein the method further comprises updating the directional inquiry as a function of a preference of the user.

19. The method of claim 18, wherein the preference of the user comprises a type of work experience.

20. The method of claim 11, wherein transmitting the directional inquiry response to the user further comprises a plurality of hyperlinks as a function of the directional inquiry response.

* * * * *